United States Patent [19]

Sugishima et al.

[11] Patent Number: 5,385,648

[45] Date of Patent: Jan. 31, 1995

[54] PROCESS FOR PREPARING A CERIC ION-CONTAINING AQUEOUS ACID SOLUTION

[75] Inventors: Noboru Sugishima; Noriaki Ikeda; Koichi Yamamoto; Yasuhiko Kizu, all of Himeji, Japan

[73] Assignee: Nippon Shokubai Co., Ltd., Osaka, Japan

[21] Appl. No.: 95,201

[22] Filed: Jul. 22, 1993

[30] Foreign Application Priority Data

Jul. 28, 1992 [JP] Japan ................... 4-201070

[51] Int. Cl.$^6$ ................... C07C 50/12; C25B 3/00
[52] U.S. Cl. ................... 204/59 R; 204/78; 204/93; 204/130
[58] Field of Search ................... 204/78, 59 R, 93, 130

[56] References Cited

U.S. PATENT DOCUMENTS

| | | | |
|---|---|---|---|
| 3,486,992 | 12/1969 | Frye | 204/86 |
| 4,638,038 | 7/1987 | Oehr | 204/93 |
| 4,639,298 | 1/1987 | Kreh et al. | 204/59 R |
| 4,647,349 | 3/1987 | Kreh et al. | 204/59 R |
| 4,670,108 | 6/1987 | Kreh et al. | 204/59 R |
| 4,701,245 | 10/1987 | Kreh | 204/78 |

FOREIGN PATENT DOCUMENTS 41561 12/1970 Japan.
013879 1/1992 Japan.

*Primary Examiner*—John Niebling
*Assistant Examiner*—Arun Phasge
*Attorney, Agent, or Firm*—Sherman and Shalloway

[57] ABSTRACT

In processes for preparing a ceric ion-containing aqueous acid solution by electrolytically oxidizing cerous ions in a cerous ion-containing aqueous acid solution using a diaphragm-free electrolytic bath having no diaphragm between the anode and the cathode, a process for preparing a ceric ion-containing aqueous acid solution which comprises making at least one heterocyclic compound selected from the group consisting of five-membered heteromonocyclic compounds having substituent(s), six-membered heteromonocyclic compounds having substituent(s) and condensed heteropolycyclic compounds exist in the cerous ion-containing aqueous acid solution.

28 Claims, No Drawings

PROCESS FOR PREPARING A CERIC ION-CONTAINING AQUEOUS ACID SOLUTION

This invention relates to a process for preparing a ceric ion-containing aqueous acid solution, a useful oxidizing agent. Detailedly, this invention relates to a process for preparing a ceric ion-containing aqueous acid solution which comprises electrolytically oxidizing a cerous ion-containing aqueous acid solution, using a diaphragm-free electrolytic bath having no diaphragm between the anode and the cathode.

A ceric ion-containing aqueous acid solution is used as an oxidizing agent for various oxidation reactions in the field of organic synthesis, for example a reaction to oxidize an aromatic compound to the corresponding quinone, e.g. a reaction to oxidize 2-methylnaphthalene to 2-methyl-1,4-naphthoquinone (vitamin $K_3$) or a reaction to oxidize naphthalene to 1,4-naphthoquinone; a reaction to oxidize a substituent of an aromatic compound, e.g. a reaction to oxidize toluene to benzaldehyde; a ring opening reaction of a cycloalkane; a reaction to carbonylate an oxime.

When an organic compound is oxidized using ceric ions, ceric ions are reduced to cerous ions, and thus it is industrially necessary to reutilize the cerous ions by recovering them and oxidizing them to regenerate ceric ions. For this purpose, an indirect electrolytic method is often carried out wherein a step to oxidize an organic compound is combined with a step to regenerate ceric ions by electrochemically oxidizing the recovered cerous ions. This invention is particularly useful as a method for regenerating ceric ions by oxidizing cerous ions to them, in such an indirect electrolytic method.

Heretofore, in methods to electrolytically oxidize cerous ions to ceric ions, a diaphragm type electrolytic bath having a diaphragm between the anode and the cathode have been used (for example, refer to Japanese Patent Publication No. 41561/1970). This is because, if there is no diaphragm, part of ceric ions once formed at the anode are reduced at the cathode to cerous ions back again and the current efficiency extremely lowers. However, when a diaphragm type electrolytic bath is used, there are problems, for example, that the structure of the electrolytic bath becomes complicated, expense for the installation of the apparatus and the diaphragm and expense for the maintenance thereof increase, and the electrolytic voltage increases due to the electric resistance of the diaphragm. Further, when organic substances are contained in the anolyte, there arise problems, for example, that the organic substances move from the anolyte to the catholyte through the diaphragm and are subject to reduction reaction, and as a result, the catholyte colors, the current efficiency lowers and the electrolytic voltage increases.

On the other hand, methods to use a diaphragm-free electrolytic bath equipped with no diaphragm are studied, and methods are proposed to oxidize electrolytically cerous ions to ceric ions while it is prevented that the ceric ions formed at the anode are rereduced at the cathode, by making the area of the cathode smaller than the area of the anode and making the current density of the cathode larger than that of the anode (for example, U.S. Patent No. 4,683,038, Japanese Laid-Open Patent, Publication No. 13879/1992, etc.). However, in these methods, there are inconveniences, for example, that since the current density of the cathode is made to be higher than that of the anode, the electrolytic voltage increases, resinous sticky matters deposit on the cathode, or the current distribution in the electrolyte tends to be ununiform. Intense stirring is necessary for the avoidance of these inconveniences, but in that case the load of power cost get larger compared with the reduction of costs due to the improvement of electrolytic characteristics. Further, there are further problems, for example, that in order to enlarge the ratio of the cathodic current density to the anodic current density, it is necessary to change largely the sizes and shapes of the electrodes.

Processes which have hitherto been proposed to prepare an aqueous acid solution of ceric ions by electrolytically oxidizing an aqueous acid solution of cerous ions have various problems as industrial-scale processes, regardless of use of any of a diaphragm type electrolytic bath and a diaphragm-free electrolytic bath.

Thus, the object of this invention lies in providing, in preparation processes wherein a diaphragm-free electrolytic bath, a process capable of preparing industrially advantageously an aqueous acid solution of ceric ions with high current efficiency without causing the lowering of the current efficiency with time lapse.

While the present inventors intensely studied on a process to regenerate an aqueous acid solution of ceric ions by electrolytically oxidizing an aqueous acid solution of cerous ions after use using a diaphragm-free electrolytic bath, they found that organic compounds present in the aqueous acid solution of cerous ions caused various undesirable influences such as the coloring of the electrolyte and the lowering of the current efficiency. Thus, the present inventors investigated in detail, e.g. on influence which various organic substances give the electrolytic characteristics, and as a result, they found that when a specific heterocyclic compound was made to coexist with cerous ions, the current efficiency was remarkably improved and further the lowering of the current efficiency with time lapse was not caused, and completed this invention. Further, they found that when this specific heterocyclic compound was made to coexist, an aqueous acid solution of ceric ions could be prepared with a high current efficiency even in the case of the electrolytic oxidation of a fresh aqueous acid solution of cerous ions.

Thus, according to this invention, there is provided in processes for preparing a ceric ion-containing aqueous acid solution by electrolytically oxidizing cerous ions in a cerous ion-containing aqueous acid solution using a diaphragm-free electrolytic bath having no diaphragm between the anode and the cathode, a process for preparing a ceric ion-containing aqueous acid solution which comprises making at least one heterocyclic compound selected from the group consisting of five-membered heteromonocyclic compounds having substituent(s), six-membered heteromonocyclic compounds having substituent(s) and condensed heteropolycyclic compounds exist in the cerous ion-containing aqueous acid solution.

It is surmised that when the above specific heterocyclic compound is used according to this invention, the compound itself stably adsorbs on the cathode surface due to the electric field applied during the electrolysis, or chemical species such as organic compounds or organic compound ions newly formed by oxidation or reduction or the like of the heterocyclic compound stably adsorb on the cathode surface, and as a result an aqueous acid solution containing eerie ions can be obtained with a high current efficiency, without a large change of the ratio of the anodic current density to the cathodic current density, and even in an electrolytic condition such that the current densities of the cathode and the anode are the same. The above stable adsorption of the above compound itself and/or the chemical species on the cathode surface not only includes a state such that these compound itself and/or chemical species are strongly adsorbing on the cathode, but includes a state such that the compound itself and/or the chemical species exist in a merely gathered state on the cathode surface, or a state such that the compound itself and/or the chemical species in the electrolyte exist while keeping an equilibrium state with the compound itself and/or the chemical species adsorbing on the cathode surface. Further, it causes no inconvenience if above compound itself and/or chemical species separate from the cathode surface at the time of the completion of electrolysis. In order to prevent the lowering of the current efficiency in the formation of ceric ions, the specific heterocyclic compound used in this invention is desirably one which does not react easily with ceric ions formed at the anode.

As the cerous ion-containing aqueous acid solution used in this invention, an aqueous sulfuric acid solution or aqueous methanesulfonic acid solution containing cerous ions is preferred, and there can, for example, be mentioned an aqueous sulfuric acid solution containing cerous sulfate, an aqueous methanesulfonic acid solution containing cerous methanesulfonate, or a mixture thereof, or the like. Further, an aqueous nitric acid solution containing cerous nitrate or the like can be used, too. Further, a cerous ion-containing aqueous acid solution is also preferable formed in a reaction to oxidize an aromatic compound to the corresponding quinone, e.g. a reaction to oxidize 2-methylnapthalene to 2-methyl-1,4-naphthoquinone (vitamin $K_3$) or a reaction to oxidize naphthalene to 1,4-naphthoquinone.

As for the concentration of cerous ions in the aqueous acid solution, if it is too low, productivity is bad and in addition the current efficiency lowers, which is industrially disadvantageous. Therefore, the concentration is preferably 0.05 mole/liter or more, more preferably in the range of 0.05-10 moles/liter.

Further, as for the acid concentration in the aqueous acid solution, it depends on the kind of the acid to be used, but generally, when the acid concentration is too low, ceric ions get unstable and when it is too high, the solubility of cerous ions lowers or corrosion of the apparatus occurs. Therefore, it is desirable that the acid concentration in the aqueous acid solution is generally in the range of 0.1-8 moles/liter. For example, it is desirable that when sulfuric acid is used as the acid, the acid concentration is in the range of 0.1-2 moles/liter, and when nitric acid is used, it is in the range of 0.1-5 moles/liter, and when methanesulfonic acid is used, it is in the range of 1-8 moles/liter.

The heterocyclic compound used in this invention is at least one heterocyclic compound selected from the group consisting of five-membered heteromonocyclic compounds having substituent(s), six-membered heteromonocyclic compounds having substituent(s), and condensed heteropolycyclic compounds. As hereto atoms constituing the heterocycle, there can be mentioned nitrogen atoms and oxygen atoms. The heterocyclic compound can be one having both atoms at the same time in the ring structure. Specifically, there can be mentioned a furan ring (oxygen-containing heterocycle), a pyrrole ring (nitrogen-containing heterocycle), etc. as five-membered heteromonocycles; a pyridine ring (nitrogen-containing heterocycle), a morpholine ring (nitrogen-containing and oxygen-containing rings), etc. as six-membered heteromonocycles; and nitrogen-containing heterocycles having 2-3 condensed rings containing 1-2 nitrogen atoms, oxygen-containing heterocycles such as a chroman ring, etc. as condensed heteropolycycles.

As the substituent(s) which five-membered heteromonocycles or six-membered heteromonocycles have, there can be mentioned at least one selected from the group consisting of alkyl group(s) having 1 to 20 carbon atoms optionally having substituent(s), nitro group(s), carboxyl group(s), acyl group(s) having 1 to 4 carbon atoms, cyano group(s), alkoxy group(s) having 1 to 20 carbon atoms and halogen atom(s). Specifically, as alkyl groups having 1 to 20 carbon atoms, there can, for example, be mentioned a methyl group, an ethyl group, a n-propyl group, an isopropyl group, a n-butyl group, an isobutyl group, a t-butyl group, a n-octyl group, an isooctyl group, a n-decyl group, etc. These alkyl groups may partially be substituted with chlorine atom(s), bromine atom(s), fluorine atom(s) or the like. As alkoxy groups having 1 to 20 carbon atoms, there can, for example, be mentioned a methoxy group, an ethoxy group, a n-propoxy group, an isopropoxy group, a n-butoxy group, an isobutoxy group, a t-butoxy group, a n-octyloxy group, an isooctyloxy group, a n-decyloxy group, etc.

As acyl groups having 1 to 4 carbon atoms, there can, for example, be mentioned a formyl group, an acetyl group, a propionyl group, a butyryl group, an isobutyryl group, etc. As halogen atoms, there can, for example, be mentioned a chlorine atom, a bromine atom and a fluorine atom.

As nitrogen-containing heterocyclic compounds used in this invention, compounds having a condensed heterocycle such as a quinoline ring and compound having a pyridine ring or a pyrrole ring are preferred. Pyrrole and pyridine are not satisfactory in adsorptive stability on the cathode, and compounds having substituent(s) on the pyridine ring or the pyrrole ring are preferred. Compounds having a molecular weight of 80 or more are further preferred.

More specifically, there can be mentioned, as nitrogen-containing heterocyclic compounds, pyrrole derivatives having substituent(s) such as nitropyrroles and N-methylpyrrole; pyridine derivatives, for example, alkyl-substituted pyridines such as $\alpha$-, $\beta$- and Y-methylpyridine ($\alpha$-, $\beta$- and Y-picoline), pyridinecarboxylic acids such as nicotinic acid, quinolinic acid, cyanopyridines such as cyanopyridine and o-, m- and p-dicyanopyridine; quinoline derivatives such as quinoline and nitroquinoline; isoquinoline; phenanthroline; phenanthridine; indole; carbazole; acridine; phenazine; etc. Methylpyridines, pyridinecarboxylic acids, cyanopyridines, quinolinic acid, quinoline, isoquinoline, phenanthroline and phenanthridine are further preferred because they are excellent in adsorptive stability on the cathode.

As preferred examples of oxygen-containing heterocyclic compounds used in this invention, there can specifically be mentioned furan derivatives having a furan ring to which substituent(s) bound, for example, furfural, 5-nitro-2-furancarboxylic acid, furancarboxylic acid and benzofuran. Further, there can be used other condensed heterocyclic compounds such as chroman, chromene, xanthene and morpholine.

Preferably, heterocyclic compounds used in this invention have a molecular weight of 80 or more in view of adsorptive stability on the cathode. However, if the molecular weight of the heterocyclic compounds gets too large, the solubility thereof in an aqueous acid solution containing a cerium salt lowers in general, and therefore further preferred molecular weight is 80–1000.

Heterocyclic compounds used in this invention may be used alone or in combination of two or more.

It is unnecessary to especially heighten the concentration of the heterocyclic compound made to exist during electrolytic oxidation because the heterocyclic compound used in this invention stably adsorbs as it is or after formation of chemical species on the cathode surface. There is no large change on its effect in concentrations higher than a certain extent, and if the concentration is too high, there can arise a case where the electrolytic voltage increases or the current efficiency, far from increasing, lowers, and therefore, the concentration of the heterocyclic compound in the electrolyte is settled preferable 1–10,000 ppm, more preferably 10–2,000 ppm.

In case, in the practice of this invention, the heterocyclic compound to be used either evaporates, reacts with ceric ions, or causes electrode reactions on the electrodes, and is gradually consumed according to the progress of electrolysis, it is better to add it at any suitable time or continuously to the electrolyte for keeping a concentration enough to maintain the effects of this invention.

Further, it is of course be possible to use the process of this invention in a form where the heterocyclic compound is added in a fresh cerous ion-containing acid solution, but practically, the process can particularly preferably be applied in a circulatory step, e.g. as follows. Step 1: a step to obtain a ceric ion-containing aqueous acid solution containing the heterocyclic compound by electrolytically oxidizing a cerous ion-containing aqueous acid solution with the addition of the heterocyclic compound thereto. Step 2: a step to oxidize various raw material organic compounds using the ceric ion-containing aqueous acid solution containing the heterocyclic compound obtained in step 1 as an oxidizing agent. Step 3: a step to recover a cerous ion-containing aqueous acid solution containing the heterocyclic compound by separating the oxidized products from the resultant mixture in step 2. Step 4: a step to obtain a ceric ion-containing aqueous acid solution containing the heterocyclic compound by electrolytically oxidizing, as it is, the cerous ion-containing aqueous acid solution containing the heterocyclic compound recovered in step 3.

In practice of this invention, electrolyte temperature is not particularly limited, but preferably a temperature equal to or lower than the boiling point of the heterocyclic compound, and if it is too low, current efficiency lowers. Thus the electrolyte temperature is, usually, settled to be a temperature in the range from 10° C. to the boiling point of the heterocyclic compound used.

Although, in general, when the current density is high, it is possible to raise the productive amount per unit electrolytic bath, there can be a case, on the other hand, where it causes lowering of the current efficiency or increase of the electrolytic voltage, or causes decomposition of the heterocyclic compound in the electrolytic solution. In practice of this invention, anodic current density is preferably settled to be 5–50 A/dm$^2$.

As stated above, in the case of the use of a diaphragm-free electrolytic bath, it is generally carried out to make the area of the cathode smaller than the area of the anode and make the cathodic current density higher than the anodic current density. However in practice of this invention, there is no need to make the ratio of the cathodic current density to the anodic current density as large as in the usual methods, and the ratio of 2 or less is adequate and the ratio of 1 will do, too.

As for the linear velocity of the electrolyte to the electrodes in the electrolytic bath, if it is too low, the current efficiency lowers or the electrolytic voltage increases and if it is too high, pressure loss in the electrolytic bath increases and troubles such as liquid spill and the increase of power cost occur, and therefore, the electrolytic solution linear velocity is preferably settled to be 1–100 cm/sec.

As the anode in this invention, the same known electrode materials as in the usual diaphragm method are used. For example, there can be used oxide-coated electrodes such as iridium oxide-coated titanium, platinumiridium oxide-coated titanium and lead dioxide-coated titanium, and platinum-plated titanium, titanium oxide, tin oxide, graphite, glassy carbon, etc. However, in consideration of current efficiency and electrode durability under the condition of containing an organic compound, it is preferable that the electrode is one containing at least one selected from lead, platinum iridium tin and tantalum. A known electrode is used as the cathode, too. However, in consideration of current efficiency and electrode durability under the condition of containing an organic substance, particularly preferred is an electrode containing at least one selected from titanium, titanium oxide, zirconium tungsten, thallium and tantalum, or an electrode based thereon.

As for the form of the electrolytic bath, industrially a filter press type electrolytic bath or a cylindrical electrolytic bath is used in general, but there is no particular limitation in practice of this invention. There can be carried out either batch type electrolysis which comprises supplying a cerous ion-containing aqueous acid solution into an electrolyte storage tank, feeding it into an electrolytic bath through an outer circulating line, and electrically oxidizing it until the ceric ion concentration of the liquid in the electrolyte storage tank gets to be a predetermined concentration, or continuous type electrolysis which comprises continuously feeding a cerous ion-containing aqueous acid solution into an electrolytic bath. The former makes electrolysis with a high current efficiency possible, but the exchange of electrolyte gets to be necessary after the completion of electrolysis, and the apparatus and instrumentation equipments get complicated. The latter makes continuous operation possible and makes the apparatus and instrumentation equipments simple, and thus is an advantageous method for industrial practice. Although, usually, there is a problem that in the case of the latter the current efficiency strikingly lowers compared with the former, high current efficiency can be obtained in this invention.

This invention is detailedly described below by examples, but not limited thereto.

EXAMPLE 1

A solution (β-picolinic acid concentration=1000 ppm) obtained by dissolving β-picolinic acid (nicotinic acid) in 10 kg of an aqueous sulfuric acid solution of cerous sulfate (containing 0.3 mole/liter cerous ions and 1.5 moles/liter of sulfuric acid as a free acid) was circulated through a filter press type diaphragm-free electrolytic cell under the following conditions, and thereby batch electrolytic oxidation was carried out until the ceric ion concentration became 0.1 mole/liter. The resultant current efficiency was 99%.

Heterocyclic compound added: β-picolinic acid (molecular weight=123, concentration=1,000 ppm)
 Electrolyte temperature: 50° C.
 Anode: Platinum-plated titanium plate electrode
  Current density 10 A/dm$^2$
 Cathode: Zirconium plate electrode
  Current density 10 A/dm$^2$
 Current density ratio (cathode/anode): 1
 Linear velocity: 30 cm/sec

Comparative Example 1

Electrolysis was carried out under the same conditions as in Example 1 except for no addition of β-picolinic acid. The resultant current efficiency was 58%.

EXAMPLE 2

Electrolytic oxidation was carried out in the same manner as in Example 1 except that the following heterocyclic compound, electrode materials and electrolytic conditions were substituted. The resultant current efficiency was 94%.

Heterocyclic compound added: Quinolinic acid (molecular weight=167, concentration=500 ppm)
 Electrolyte temperature: 60° C.
 Anode: Iridium-tin mixed oxide-coated titanium plate electrode
  Current density 10 A/dm$^2$
 Cathode: Tungsten plate electrode
  Current density 10 A/dm$^2$
 Current density ratio (cathode/anode): 1
 Linear velocity: 50 cm/sec

EXAMPLE 3

Electrolytic oxidation was carried out in the same manner as in Example 1 except that the following heterocyclic compound, electrode materials and electrolytic conditions were substituted. The resultant current efficiency was 97%.

Organic compound added: β-picoline (molecular weight=93, concentration=1,500 ppm)
 Electrolyte temperature: 50° C.
 Anode: Lead dioxide-coated titanium plate electrode
  Current density 30 A/dm$^2$
 Cathode: Zirconium-expanded electrode
  Current density 50 A/dm$^2$
 Current density ratio (cathode/anode): 1.67
 Linear velocity: 40 cm/sec

EXAMPLE 4

Electrolytic oxidation was carried out in the same manner as in Example 1 except that the following heterocyclic compound, electrode materials and electrolytic conditions were substituted. The resultant current efficiency was 98%.

Heterocyclic compound added: Quinoline (molecular weight=129, concentration=3,000 ppm)
 Electrolyte temperature: 50° C.
 Anode: Iridium oxide-platinum-coated titanium-expanded electrode
  Current density 10 A/dm$^2$
 Cathode: Zirconium-expanded electrode
  Current density 10 A/dm$^2$
 Current density ratio (cathode/anode): 1
 Linear velocity: 20 cm/sec

Comparative Example 2

Electrolytic oxidation was carried out in the same manner as in Example 1 except that the following heterocyclic compound, electrode materials and electrolytic conditions were substituted. Current efficiency was 78%.

Heterocyclic compound added: Pyridine (molecular weight=79, concentration=1,000 ppm)
 Electrolyte temperature: 50° C.
 Anode: Iridium oxide-coated titanium plate electrode
  Current density 10 A/dm$^2$
 Cathode: Tungsten plate electrode
  Current density 10 A/dm$^2$
 Current density ratio (cathode/anode): 1
 Linear velocity: 20 cm/sec

Comparative Example 3

Electrolysis was carried out under the same conditions as in Comparative example 2 except for no addition of pyridine. The resultant current efficiency was 60%.

Comparative Example 4

Electrolysis was carried out under the same conditions as in Comparative example 2 except that the concentration of pyridine was changed to 50,000 ppm. The resultant current efficiency was 47%.

Comparative Example 5

Electrolysis was carried out under the same conditions as in Comparative example 2 except for addition of o-xylene (molecular weight=106, concentration=1,000 ppm). The resultant current efficiency was 53%.

EXAMPLE 5

Electrolytic oxidation was carried out in the same manner as in Example 1 except that the following heterocyclic compound, electrode materials and electrolytic conditions were substituted. The resultant current efficiency was 97%.

Heterocyclic compound added: Isoquinoline (molecular weight=129, concentration=100 ppm)
 Electrolyte temperature: 40° C.
 Anode: Iridium-tantalum mixed oxide-coated titanium plate electrode
  Current density 15 A/dm$^2$
 Cathode: Zirconium plate electrode
  Current density 15 A/dm$^2$
 Current density ratio (cathode/anode): 1
 Linear velocity: 40 cm/sec

EXAMPLE 6

Electrolytic oxidation was carried out in the same manner as in Example 1 except that β-picolinic acid was added so that its concentration become 20,000 ppm. The resultant current efficiency was 91%.

EXAMPLE 7

Electrolysis was carried out under the same conditions as in Example 1 except that the concentration of β-picolinic acid was made to be 5 ppm. The resultant current efficiency was 80%.

EXAMPLE 8

Electrolysis was carried out under the same conditions as in Example 1 except that the concentration of β-picolinic acid was made to be 10 ppm. The resultant current efficiency was 96%.

EXAMPLE 9

Electrolysis was carried out under the same conditions as in Example 1 except that the concentration of β-picolinic acid was made to be 5,000 ppm. The resultant current efficiency was 95%.

EXAMPLE 10

A solution (1,10-phenanthroline concentration=50 ppm) obtained by dissolving 1,10-phenanthroline in 10 kg of an aqueous sulfuric acid solution of cerous sulfate containing ceric sulfate (containing 0.4 mole/liter cerous ions, 0.25 mole/liter ceric ions and 1.0 mole/ liter sulfuric acid as a free acid) was circulated through a filter press type diaphragm-free electrolytic cell under the following conditions, and thereby batch electrolytic oxidation was carried out until the ceric ion concentration became 0.45 mole/liter. The resultant current efficiency was 99%.

Heterocyclic compound added: 1,10-phenanthroline (molecular weight=180, concentration=50 ppm)
Electrolyte temperature: 50° C.
Anode: Platinum-plated titanium plate electrode
Current density 10 A/dm$^2$
Cathode: Zirconium plate electrode
Current density 10 A/dm$^2$
Current density ratio (cathode/anode): 1
Linear velocity: 30 cm/sec

EXAMPLE 11

Electrolytic oxidation was carried out in the same manner as in Example 10 except that the following heterocyclic compound, electrode materials and electrolytic conditions were substituted. The resultant current efficiency was 89%.

Heterocyclic compound added: Furfural (molecular weight=96, concentration=1,000 ppm)
Electrolyte temperature: 50° C.
Anode: Lead dioxide-coated titanium plate electrode
Current density 20 A/dm$^2$
Cathode: Tungsten plate electrode (the surface being partly coated with a resin)
Current density 30 A/dm$^2$
Current density ratio (cathode/anode): 1.5
Linear velocity: 50 cm/sec

EXAMPLE 12

Electrolytic oxidation was carried out in the same manner as in Example 11 except that the following heterocyclic compound, electrode materials and electrolytic conditions were substituted. The resultant current efficiency was 98%.

Heterocyclic compound added: 5-nitro-2-furancarboxylic acid (molecular weight=157, concentration=1,000 ppm)
Electrolyte temperature: 50° C.
Anode: Iridium oxide-coated titanium plate electrode
Current density 10 A/dm$^2$
Cathode: Zirconium plate electrode
Current density 10 A/dm$^2$
Current density ratio (cathode/anode): 1
Linear velocity: 20 cm/sec

EXAMPLE 13

A solution (phenanthridine concentration=1,000 ppm) obtained by dissolving phenanthridine in 10 kg of an aqueous nitric acid solution of cerous nitrate (containing 2.0 moles/liter cerous ions and 1.0 mole/liter nitric acid as a free acid) was circulated through a filter press type diaphragm-free electrolytic cell under the following conditions, and thereby batch electrolytic oxidation was carried out until the ceric ion concentration became 0.1 mole/liter. The resultant current efficiency was 88%.

Heterocyclic compound added: Phenanthridine (molecular weight=179, concentration=1,000 ppm)
Electrolyte temperature: 50° C.
Anode: Iridium oxide-coated titanium plate electrode
Current density 10 A/dm$^2$
Cathode: Zirconium plate electrode
Current density 10 A/dm$^2$
Current density ratio (cathode/anode): 1
Linear velocity: 20 cm/sec

Comparative Example 6

Electrolysis was carried out under the same conditions as in Example 13 except that the phenanthridine was not added. The resultant current efficiency was 43%.

EXAMPLE 14

A solution (cyanopyridine concentration=1,000 ppm) obtained by dissolving cyanopyridine in 10 kg of an aqueous methanesulfonic acid solution of cerous methanesulfonate (containing 1.7 moles/liter cerous ions and 1.6 mole/liter methanesulfonic acid as a free acid) was circulated through a filter press type diaphragm-free electrolytic cell under the following conditions, and thereby batch electrolytic oxidation was carried out until the ceric ion concentration became 0.1 mole/liter. The resultant current efficiency was 98%.

Heterocyclic compound added: Cyanopyridine (molecular weight=104, concentration=1,000 ppm)
Electrolyte temperature: 50° C.
Anode: Iridium oxide-coated titanium plate electrode
Current density 10 A/dm$^2$
Cathode: Zirconium plate electrode
Current density 10 A/dm$^2$
Current density ratio (cathode/anode): 1
Linear velocity: 20 cm/sec

Comparative Example 7

Electrolysis was carried out under the same conditions as in Example 14 except that cyanopyridine was not added.

EXAMPLE 15

23.7 g of 2-methylnaphthalene and 100 g of o-xylene were feeded and stirred in a glass-made reactor equipped with a reflux condenser and a stirring apparatus to give a solution, 10 liters of the aqueous acid solution containing 0.2 mole/liter cerous sulfate and 0.1 mole/liter ceric sulfate prepared in Example 1 was added, and the mixture was subjected to reaction at 50° C. for 2 hours. After the completion of the reaction, stirring was discontinued, the reaction mixture was moved to a separating vessel, and the o-xylene phase and the aqueous layer were separated. The aqueous phase was extracted with 100 g of o-xylene and the extract was added to the above solvent phase. As a result of the analyses of the o-xylene phase and the aqueous phase, the conversion of the raw material 2-methylnaphthalene was 95%, the selectivity of 2-methyl-1,4-naphthoquinone (vitamin $K_3$) was 72%, the selectivity of 6-methyl-1,4-naphthoquinone was 25% and the selectivity of o-phthalic acid was 2%. 2-methylnapthalene, 2-methyl-1,4-naphthoquinone and 6-methyl-1,4-naphthoquinone existed only in the o-xylene phase, and o-phthalic acid existed only in the aqueous phase. Further, in the aqueous phase, the concentration of cerous sulfate was 0.298 mole/liter, the concentration of ceric sulfate was 0.002 mole/liter and the concentration of o-phthalic acid was 53 ppm, and the concentration of $\beta$-picolinic acid added in Example 1 remained 1,000 ppm and did not change. When 10 liters of this aqueous phase was subjected to electrolysis under the same conditions as in Example 1, a current efficiency of 99%, as in Example 1, was obtained.

EXAMPLE 16

21.3 g of naphthalene and 100% of o-xylene were feeded and stirred in a glass-made reactor equipped with a reflux condenser and a stirring apparatus to give a solution, 10 liters of the aqueous acid solution containing 0.2 mole/liter cerous sulfate and 0.1 mole/liter ceric sulfate prepared in Example 2 was added, and the mixture was subjected to reaction at 50° C. for 1 hours. After completion of the reaction, stirring was discontinued, the reaction was moved to a separating vessel, and the o-xylene phase and the aqueous phase were separated. The aqueous phase was extracted with 100 g of o-xylene and the extract was added to the above solvent phase. As a result of the analyses of the o-xylene phase and the aqueous phase, the conversion of the raw material naphthalene was 96%, the selectivity of 1,4-naphthoquinone was 95%, and the selectivity of o-phthalic acid was 2%. Naphthalene and 1,4-naphthoquinone existed only in the o-xylene phase, and o-phthalic acid existed only in the aqueous phase. Further, in the aqueous phase the concentration of cerous sulfate was 0.295 mole/liter, the concentration of ceric sulfate was 0.005 mole/liter and the concentration of o-phthalic acid was 53 ppm, and the concentration of quinolinic acid added in Example 2 remained 1,000 ppm and did not change. 10 Liters of this aqueous phase was subjected to electrolysis under the same conditions as in Example 2, and as a result a current efficiency of 95% was obtained.

EXAMPLE 17

28.8 g of 1-nitronaphthalene, and 10 liters of the aqueous acid solution containing 1.9 moles/liter cerous nitrate and 0.1 mole/liter ceric nitrate prepared in Example 13 were feeded in a glass-made reactor equipped with a reflux condenser and a stirring apparatus, and the mixture was warmed to 70° C. to dissolve 1-nitronaphthalene, stirred and subjected to reaction for 1 hour. After completion of the reaction, 100 g of nitrobenzene was added, the mixture was stirred for 5 minutes, stirring was discontinued, the reaction solution was moved to a separating vessel, and the nitrobenzene phase and the aqueous phase were separated. The aqueous phase was extracted with 100 g of nitrobenzene and the extract was added to the above solvent phase. As a result of the analyses of the nitrobenzene phase and the aqueous phase, the conversion of the raw material 1-nitronaphthalene was 80%, the selectivity of 5-nitro-1,4-naphthoquinone was 90%, the selectivity of 3-nitrophthalic acid was 2%, the selectivity of 4-nitrophthalic acid was 3%, and the selectivity of o-phthalic acid was 5%. 1-nitronaphthalene and 5-nitro-1,4-naphthoquinone existed only in the nitrobenzene phase, and 3-nitrophathalic acid, 4-nitrophthalic acid and o-phthalic acid existed only in the aqueous phase. Further, in the aqueous phase, the concentration of cerous nitrate was 1.996 mole/liter, the concentration of ceric nitrate was 0.004 mole/liter, the concentration of o-phthalic acid was 110 ppm, and the concentration of 3-nitrophthalic acid and 4-nitrophthalic acid was 140 ppm in total, and the concentration of phenanthridine added in Example 13 was 900 ppm. 10 Liters of the aqueous phase was subjected to electrolysis under the same conditions as in Example 13, and as a result a current efficiency of 87% was obtained.

We claim:

1. A process for preparing a ceric ion-containing aqueous acid solution by electrolytically oxidizing cerous ions in a cerous ion-containing aqueous acid solution contained in an electrolytic bath having no diaphragm between the anode and the cathode, which process comprises adding in an amount of 1 to less than 20,000 ppm at least one heterocyclic compound selected from the group consisting of substituted five-membered heteromonocyclic compounds, substituted six-membered heteromonocyclic compounds and condensed heteropolycyclic compounds to the cerous ion-containing aqueous acid solution, and electrolytically oxidizing said cerous ions to ceric ions.

2. The process according to claim 1 wherein the substituent of the five-membered heteromonocyclic compound and the six-membered heteromonocyclic compound is at least one seleted from the group consisting of alkyl groups having 1 to 20 carbon atoms, nitro groups, carboxyl groups, acyl groups having 1 to 4 carbon atoms, cyano groups, alkoxy groups having 1 to 20 carbon atoms and halogen atoms.

3. The process according to claim 1 wherein the heterocyclic compound is a nitrogen-containing heterocyclic compound having a molecular weight of 80 or more.

4. The process according to claim 3 wherein the nitrogen-containing heterocyclic compound is at least one selected from the group consisting of methylpyridine, pyridinecarboxylic acid, cyanopyridine, quinolinic acid, quinoline, isoquinoline, phenanthroline and phenanthridine.

5. The process according to claim 1 wherein the heterocyclic compound is an oxygen-containing heterocyclic compound having a furan ring.

6. The process according to claim 5 wherein the oxygen-containing heterocyclic compound is at least one selected from the group consisting of furfural and 5-nitro-2-furancarboxylic acid.

7. The process according to claim 1 wherein the heterocyclic compound is added in an amount to maintain a concentration of 1 to 10,000 ppm in the aqueous acid solution.

8. The process according to claim 7 where the heterocyclic compound is added in an amount to maintain a concentration of 10 to 2,000 pm in the aqueous acid solution.

9. The process according to claim 1 wherein cerous ions are added in an amount of 0.05–10 moles/liter to the aqueous acid solution.

10. The process according to claim 1 wherein the aqueous acid solution is selected from the group consisting of an aqueous sulfuric acid solution, an aqueous methanesulfonic acid solution and a mixture thereof.

11. The process according to claim 1 wherein the current density at the anode is in the range of 5–50 A/dm$^2$, and the current density at the cathode is in the range of one to two times the current density at the anode.

12. The process according to claim 1 wherein the cerous ion-containing aqueous acid solution is one produced by a reaction to oxidize an organic compound with the ceric ion-containing aqueous acid solution.

13. The process according to claim 12 wherein the reaction to oxidize the organic compound is a reaction to oxidize 2-methylnaphthalene to 2-methyl-1,4-naphthoquinone.

14. A process for preparing a ceric ion-containing aqueous acid solution by electrolytically oxidizing cerous ions in a cerous ion-containing aqueous acid solution contained in an electrolytic bath having no diaphragm between the anode and the cathode, which process comprises adding in an amount of 5 to 10,000 ppm at least one heterocyclic compound selected from the group consisting of substituted five-membered heteromonocyclic compounds, substituted six-membered heteromonocyclic compounds and condensed heteropolycyclic compounds to the cerous ion-containing aqueous acid solution, wherein the substituent of the five-membered heteromonocyclic compound and the six-membered heteromonocyclic compound is at least one selected from the group consisting of alkyl groups having 1 to 20 carbon atoms, nitro groups, carboxyl groups, acyl groups having 1 to 4 carbon atoms, cyano groups, alkoxy groups having 1 to 20 carbon atoms and halogen atoms, and electrolytically oxidizing said cerous ions to ceric ions.

15. The process according to claim 14 wherein the nitrogen-containing heterocyclic compound is at least one selected from the group consisting of methylpyridine, pyridinecarboxylic acid, cyanopyridine, quinolinic acid, quinoline, isoquinoline, phenanthroline and phenanthridine.

16. The process according to claim 14 wherein the heterocyclic compound is an oxygen-containing heterocyclic compound having a furan ring.

17. The process according to claim 16 wherein the oxygen-containing heterocyclic compound is at least one selected from the group consisting of furfural and 5-nitro-2-furancarboxylic acid.

18. The process according to claim 14 wherein the heterocyclic compound is added in an amount to maintain a concentration of 5 to 2,000 ppm in the aqueous acid solution.

19. The process according to claim 14 wherein the cerous ion-containing aqueous acid solution is one produced by a reaction to oxidize an organic compound with the ceric ion-containing aqueous acid solution.

20. The process according to claim 19 wherein the reaction to oxidize the organic compound is a reaction to oxidize 2methylnaphthalene to 2-methyl-1,4-naphthoquinone.

21. A process for preparing a ceric ion-containing aqueous acid solution by electrolytically oxidizing cerous ions in a cerous ion-containing aqueous acid solution contained in an electrolytic bath having no diaphragm between the anode and the cathode, which process comprises the steps of (A) adding in an amount of 1 to less than 20,000 ppm at least one heterocyclic compound selected from the group consisting of substituted five-membered heteromonocyclic compounds, substituted six-membered heteromonocyclic compounds and condensed heteropolycyclic compounds to the cerous ion-containing aqueous acid solution, wherein the substituent of the five-membered heteromonocyclic compound is at least one selected from the group consisting of alkyl groups having 1 to 20 carbon atoms, nitro groups, carboxyl groups, acyl groups having 1 to 4 carbon atoms, cyano groups, alkoxy groups having 1 to 20 carbon atoms and halogen atoms, and electrolytically oxidizing said cerous ions to ceric ions, (B) adding the aqueous acid solution of ceric ions and heterocyclic compound to a solution of an organic compound dissolved in an organic solvent and oxidizing said organic compound to obtain a reaction mixture containing an oxidized organic compound and an aqueous acid solution comprising cerous ions and said heterocyclic compound, (C) separating the oxidized organic compound and organic solvent from the aqueous acid solution comprising cerous ions and said heterocyclic compound, and (D) electrolytically oxidizing said cerous ions to ceric ions.

22. The process according to claim 21 wherein the oxidizing step (B) is carried out with an oxidizing agent which consists essentially of ceric ions and said heterocyclic compound.

23. The process according to claim 21 wherein the nitrogen-containing heterocyclic compound is at least one selected from the group consisting of methylpyridine, pyridinecarboxylic acid, cyanopyridine, quinolinic acid, quinoline, isoquinoline, phenanthroline and phenanthridine.

24. The process according to claim 21 wherein the heterocyclic compound is an oxygen-containing heterocyclic compound having a furan ring.

25. The process according to claim 24 wherein the oxygen-containing heterocyclic compound is at least one selected from the group consisting of furfural and 5-nitro-2-furancarboxylic acid.

26. The process according to claim 21 wherein the heterocyclic compound is added in an amount to maintain a concentration range of 5 to 10,000 ppm in the aqueous acid solution.

27. The process according to claim 21 where the heterocyclic compound is added in an amount to maintain a concentration range of 5 to 2,000 ppm in the aqueous acid solution.

28. The process according to claim 21 wherein the reaction to oxidize the organic compound is a reaction to oxidize 2-methylnaphthalene to 2-methyl-1,4-naphthoquinone.

* * * * *